United States Patent
Berner

(10) Patent No.: US 7,312,874 B2
(45) Date of Patent: Dec. 25, 2007

(54) APPARATUS AND A METHOD FOR DETERMINING THE COLOR STIMULUS SPECIFICATION OF TRANSLUCENT OBJECTS

(75) Inventor: Markus Berner, Niederhasli (CH)

(73) Assignee: MHT Optic Research AG, Niederhasli (CH)

( * ) Notice: Subject to any disclaimer, the term of this patent is extended or adjusted under 35 U.S.C. 154(b) by 107 days.

(21) Appl. No.: 11/173,272

(22) Filed: Jul. 1, 2005

(65) Prior Publication Data

US 2006/0023215 A1    Feb. 2, 2006

(30) Foreign Application Priority Data

Jul. 29, 2004   (CH)   ................................... 01276/04

(51) Int. Cl.
*G01J 3/46* (2006.01)
(52) U.S. Cl. ....................... 356/402; 356/405; 356/416; 356/420
(58) Field of Classification Search ................ 356/402, 356/405, 416, 420
See application file for complete search history.

(56) References Cited

U.S. PATENT DOCUMENTS

| | | | |
|---|---|---|---|
| 5,241,170 A | 8/1993 | Field, Jr. et al. | |
| 5,963,333 A | 10/1999 | Walowit et al. | |
| 6,038,024 A | * 3/2000 | Berner | ........................ 356/326 |
| 6,525,819 B1 | 2/2003 | Delawter et al. | |
| 2005/0254704 A1* | 11/2005 | Komiya et al. | ............. 382/162 |

FOREIGN PATENT DOCUMENTS

| | | |
|---|---|---|
| DE | 10256188 | 6/2004 |
| EP | 0928957 | 7/1999 |

OTHER PUBLICATIONS

European Search Report for Application 05405406.9, dated Nov. 11, 2005.

* cited by examiner

*Primary Examiner*—Roy M. Punnoose
(74) *Attorney, Agent, or Firm*—Maginot, Moore & Beck

(57) ABSTRACT

The Apparatus for determining the color stimulus specification of a translucent object, for example of a tooth, comprises an illumination device as well as an image capture device. For illuminating the object under test with light in different wave length portions, the illumination device comprises an LED array with a plurality of sequentially energizable light emitting diodes. Several different types of light emitting diodes are provided, each emitting light in a different wave length portion.

17 Claims, 3 Drawing Sheets

APPARATUS AND A METHOD FOR DETERMINING THE COLOR STIMULUS SPECIFICATION OF TRANSLUCENT OBJECTS

BACKGROUND OF THE INVENTION

The present invention refers to an apparatus for determining the color stimulus specification of objects, particularly of translucent objects, comprising an illumination assembly for illuminating the object under test, a detection assembly for capturing the light emitted by the illumination assembly and reflected by the object under test, and an analyzer assembly adapted for evaluating the calorimetric data of the object under test. The detection assembly includes a lens assembly and at least one image sensor, and it is adapted to deliver output signal data in response to the captured light.

Moreover, the present invention also refers to a method for determining the color stimulus specification of translucent objects, in which the object under test is illuminated and the light emitted by the object under test is captured by at least one image sensor, and in which the calorimetric data of the object under test are arithmetically evaluated by means of a suitable analyzer.

PRIOR ART

U.S. Pat. No. 6,038,024 discloses a method and an apparatus for determining the color stimulus specification of translucent objects. For determining the color stimulus specification of the translucent object under test, the latter one is illuminated with light in different wave length portions, or the light reflected by the object under test is subdivided into different wave length portions prior to its capture by the image sensor. As a light source, a conventional lamp is used. For creating the different wave length portions, a concave mirror provided with a diffraction grating is inserted into the light path. By rotating the concave mirror, the wave length portion entering a subsequent light conductive fiber bundle is changed. Preferably, two image sensors are used, whereby one sensor serves for visualizing the object under test, while the other sensor is used for evaluating the colorimetric data of the object under test.

OBJECTS OF THE INVENTION

It is an object of the present invention to provide an apparatus for determining the color stimulus specification of objects, particularly of translucent objects, which is cost-efficient, light and portable. It is a further object of the present invention to provide an apparatus for determining the color stimulus specification of objects, particularly of translucent objects, in which the power consumption is reduced to such a degree that it can be operated by means of batteries.

SUMMARY OF THE INVENTION

To meet these and other objects, the present invention provides an apparatus for determining the color stimulus specification of translucent objects, comprising an illumination assembly for illuminating the object under test, and a detection assembly for capturing the light emitted by the illumination assembly and reflected by the object under test. The detection assembly includes a lens and an image sensor and is adapted to deliver output signal data in response to the captured light. Further provided are means for visualizing the output signal data delivered by the detection assembly, and a control and analyzer device adapted to evaluate the calorimetric data of the object under test.

The illumination assembly comprises a light emitting diode array including a plurality of light emitting diodes emitting light in different wave length portions. Each light emitting diode or group of light emitting diodes emitting light in a certain wave length portion is sequentially energized under the influence of the control and analyzer device.

Due to the fact that the illumination assembly comprises a plurality of light emitting diodes emitting light in different wave length portions and which are sequentially energized, the fundamental prerequisite is created to operate the apparatus autonomically, i.e. independent of a mains power supply. Even if light emitting diodes have only a slightly better efficiency than incandescent bulbs, it is ensured that, in contrast to using incandescent bulbs, the entirety of the emitted light energy of the particular wave length portion can be used for the measurement; thus, the optical efficiency is approximately 20 times higher. The result is that the power consumption is drastically reduced, rendering it possible to operate the apparatus by means of batteries, be it conventional ones, be it rechargeable ones. Using light emitting diodes instead of a conventional light source with electrically driven concave mirror has the further advantage that the apparatus is substantially smaller and lighter and can be manufactured at lower costs.

According to a further aspect of the invention, there is provided a method for determining the color stimulus specification of translucent objects, in which the object under test is illuminated and the light emitted by the object under test is captured by at least one image sensor. The calorimetric data of the object under test are arithmetically evaluated by means of a suitable analyzer means. Thereby, the illumination of the object under test comprises the steps of:

Providing a light emitting diode array including a plurality of light emitting diodes emitting light in different wave length portions;

initiating a measuring cycle;

illuminating the object under test by consecutively energizing each of the light emitting diodes emitting light in different wave length portions; and terminating the measuring cycle.

BRIEF DESCRIPTION OF THE DRAWINGS

In the following, embodiments of the apparatus according to the invention will be further described, with reference to the accompanying drawings, in which.

DETAILED DESCRIPTION OF THE PREFERRED EMBODIMENTS

Figure 1:
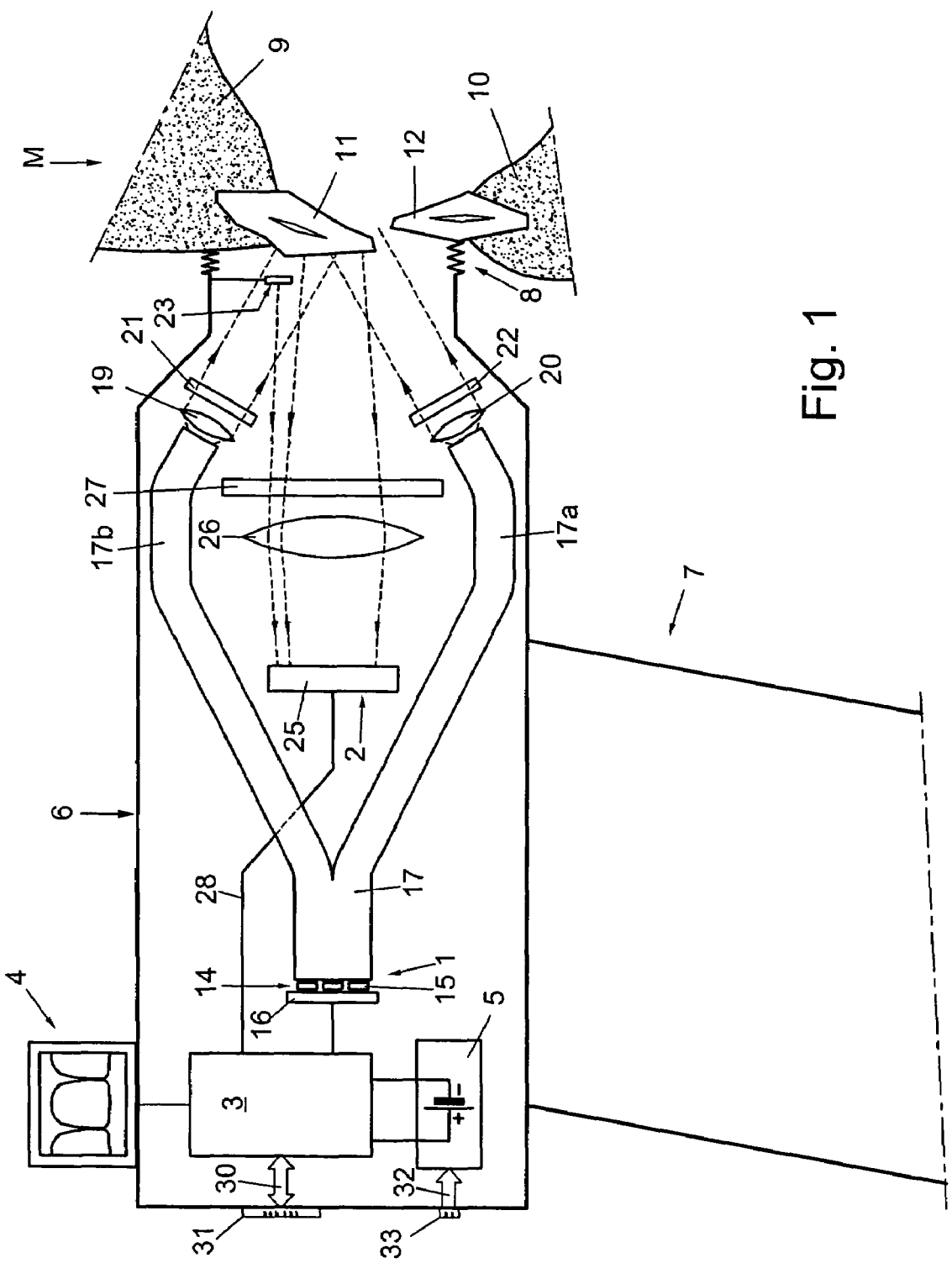
FIG. 1 shows a schematic lateral view of the apparatus.

The apparatus schematically shown in FIG. 1 essentially comprises an illumination assembly 1, a detection assembly 2, a microprocessor operated control and evaluating device 3, a display 4 and a battery 5. All the above mentioned elements are received in the interior of an upper portion of the apparatus designed as a probe head 6. The probe head 6 comprises a front portion 8, adapted to be moved towards and rest on the object under test M. The entire apparatus is designed as an autonomic, portable device and provided with a hand grip 7. In the present example, as the object under test M, portions of the upper jaw 9 and the lower jaw 10 together with two teeth 11, 12 are schematically shown.

The illumination assembly 1 comprises, as the real light source, a light emitting diode (LED) array 14 including a plurality of light emitting diodes 15; in the drawing, however, only three of them are schematically shown. In practice, it is understood that a much higher number is used. The light emitting diodes 14 are arranged on a circuit board 16. In total, the LED array 14 comprises eight different types of light emitting diodes, emitting light in eight different wavelengths. The design of the LED array 14 will be further discussed herein below in more detail.

The illumination assembly 1 further comprises a light conducting fiber bundle 17 into which the light emitted by the light emitting diodes 15 is directed. The light conducting fiber bundle 17 has the shape of a Y comprising two strands 17a and 17b. The free ends of the two strands 17a, 17b of the light conducting fiber bundle 17 both are split apart into individual fibers which are arranged along an annulus. Thus, a substantially homogenous illumination of the object under test M is achieved. At the free ends of the strands 17a, 17b, in each case a lens 19, 20 is provided, further contributing to a homogenous illumination of the object under test M. At the light output side of the lenses 19, 20, in each case a schematically shown polarizing filter 21, 22 is located. Finally, as can be seen in the drawing, a reference mark 23 is provided; the sense and function thereof will be explained in more detail herein after.

The detection assembly 2 is provided with a sensor 25 configured to capture the light reflected by the object under test M. As a sensor 25, preferably a black-and-white CCD chip sensor (CCD=Charge Coupled Device) or a black-and-white CMOS sensor is used. The sensor 25 is connected to the control and analyzer device 3 by means of a data conductor 28. In order to concentrate the light reflected by the object under test M to the surface of the sensor 25, a lens 26 is located in front of the sensor 25. In front of the lens 26, a polarization filter 27 is provided that is adjusted with regard to the polarization filters 21, 22 at the outlet side of the strands 17a, 17b in such a way that it lets pass the light emitted by the object under test M, but blocks the light reflected by the surface of the object under test M, i.e. the surface glare. To this end, the polarization filter 27 located in front of the sensor 25 has a polarizing orientation that is rotated by 90° with regard to the polarization filters 21, 22 located at the outlet of the strands 17a, 17b of the light conducting fiber bundle 17. However, it is also possible to arrange all the polarization filters 21, 22, 27 with their polarizing orientation at the same angle, but to provide one or more additional circular polarization filters.

Further, the apparatus is provided with a plug-in socket 31, connected to the control and analyzer device 3 by means of a data cable 30. By means of that plug-in socket 31, data can be bi-directionally exchanged and transmitted, respectively. Particularly, it is possible to retrieve the measured colorimetric data from the control and analyzer device 3 by means of the plug-in socket 31. Additionally, a further socket 32 is provided, connected to the battery 5 by means of a power supply line, to connect the apparatus to a battery charging device. It is understood that the expression "battery" includes all sort of batteries, be it rechargeable or not.

As already mentioned, the LED array 14 comprises eight different types of light emitting diodes. Thereby, the array 14 emits light in eight different, narrow band wavelength regions between 430 nm and 650 nm, similar to a so-called monochromator, whereby the wavelength regions shall be distributed as evenly as possible within the above mentioned range of between 430 nm and 650 nm. It is understood, rather than using eight different types of light emitting diodes, that any other number of different LED types could be used. The number of light emitting diodes depends, amongst else, on their availability as well as on the requirements of the chromatics. If, in future, other types of light emitting diodes should become available, emitting light in other wavelength regions, it would be possible to cover the entire range of visible light between approximately 380 nm and 730 nm with a corresponding number of different light emitting diodes.

While only one light emitting diode is provided for certain wavelength regions, for other wavelength regions, several, parallel connected light emitting diodes have to be provided. The reason is that not for all required wavelength regions enough powerful light emitting diodes are available. Thus, in order to be able to feed luminous flux of the required intensity into the light conduction fiber bundle 17 in all eight different wavelength regions, i.e. in order to achieve a good signal-to-noise ration, such a number of light emitting diodes being of the low output type are arranged in parallel configuration to form a light emitting diode group that the total luminous flux equals the one of a single high output light emitting diode.

The light emitting diodes 15 are arranged along an annulus on the circuit board in COB (Chip-on-Board) technology and electrically bonded to the corresponding contact surface or circuit board trace. In order to dissipate the heat generated by the light emitting diodes as efficiently as possible, preferably a metal core circuit board is used. The individual light emitting diodes are arranged on the circuit board without a case and bonded to the corresponding traces, whereby the entire LED array is potted, e.g. by means of a clear epoxy resin material, and coupled to the light conducting fiber bundle 17 by means of a further transparent mass, e.g. a silicon gel material.

The diameter of the light conducting fiber optic bundle 17 is matched to the diameter of the LED array 14 and amounts, in the present example, to less than 10 mm. Preferably, the individual, high output light emitting diodes are located more towards the center, while the low output light emitting diodes are located more towards the periphery of the array 14. In order to feed the light emitted by the LED array 14 to the light conducting fiber bundle 17 as efficiently as possible, the end of the light conducting fiber bundle 17 is located very closely to the light emitting diodes of the array 14, i.e. in a distance of less than 1 mm.

Preferably, the illumination assembly is designed in such a way that it illuminates not only the tooth 11 and 12, respectively, to be measured, but also the adjoining region of the upper jaw 9 and the lower jaw 10, respectively. In other words, based on the average size of a tooth, an area of at least 10×15 mm, preferably 16×22 mm, should be illuminated. Due to the translucent nature of the object under test (i.e. the tooth 11, 12), it is import ant that the illuminated area is larger than the area to be examined for determining the color stimulus specification, i.e. larger than the individual tooth.

For performing a measuring operation, first, a measurement without illumination by the illumination assembly 1 is done. The measured data received by the sensor 25 under these circumstances thereby corresponds to the amount of light coming from the ambient and falling onto the object under test and onto the sensor 25. In order to avoid a falsification of the measurement during the real measuring step, i.e. with engaged illuminating assembly 1, caused by the ambient light, the results of the above mentioned first measurement are subtracted from the results of the real measurement results.

Thereafter, eight consecutive measurements with illumination by the illumination device 1 are performed. Thereby, in the first of these eight measurements, only the light emitting diode or the group of light emitting diodes emitting light in a first wavelength region are switched on. In a second of these eight measurements, only the light emitting diode or the group of light emitting diodes emitting light in a second wavelength region are switched on. Correspondingly, in the remaining six measurements, the six remaining light emitting diodes or light emitting diode groups are switched on. Thus, the object under test is consecutively illuminated with visible light in eight different wavelengths. During the activation of the particular light emitting diode or group of light emitting diodes, the measurement value present at the sensor 25 is read and stored. Preferably, the light emitting diodes are energized only during a very short time, but with a multiple of their rated current. For example, the light emitting diodes can be energized only during appr. 20 ms, but with five to ten times the current rated by the manufacturer. In this way, the desired intensity of light can be reached without any danger that the light emitting diodes 15 are damaged or destroyed.

Since the luminous flux emitted by the light emitting diodes 15 is subject to certain fluctuations, in each measurement, the luminous flux reflected by the reference mark 23 is measured by the sensor 25. On the basis of the measured reference value, the emitted luminous flux can be calculated and, if appropriate, used for correcting the measurement results. The correction value is calculated as follows: Before the real measurement is taken, a number of measurements are performed for determining the amount of the light reflected by the reference mark 23. Then, an average value is calculated. If, during a real measurement of the object under test, the value of the amount of light reflected by the reference mark 23 is higher or lower than the average value calculated initially, the measuring result is corrected by a corresponding factor.

In the present example, only one reference mark 23 is shown. However, in practice, preferably at least two reference marks 23 are used. Thereby, the reference marks 23 are located as close to the front end of the front portion 8 of the probe head 6 as possible. In order not to negatively influence the size of the area to be measured, the two reference marks 23 preferably are located such that they cover only two opposite corner regions of the illuminated area.

In order to provide a sufficiently exact positioning of the probe head 6 on the object under test M, the latter one is visually displayed on the display 4. To this end, the object under test is sequentially illuminated, in very short intervals, by light in the wavelength regions of the three primary colors red, green and blue. Thereby, those three light emitting diodes or light emitting diode groups are energized that emit light as close to the three primary colors as possible. From these three pictures in red, green and blue, a color picture can be calculated in displayed on the display 4, as schematically shown in the drawing.

However, in order to get optimal and very exact measurement results, the probe head of the apparatus must be aligned with regard to the object under test such that the optical axis of the apparatus is exactly perpendicular to the surface of the object under test. In the case of a tooth located in the mouth of a person as the object under test, the above mentioned exact alignment is not so easy to realize since the operator of the apparatus cannot see the teeth during the measurement process. A further difficulty arises if the teeth are askew in the mouth, as is often the case. Since the probe head of the apparatus of the invention is manipulated by hand, i.e. simply set up on the mouth of the person whose teeth's color has to be determined, it occurs quite often that measurements are run with an angular error that is too high; tolerable is an angular error of approximately ±10°. Such angular errors mostly occur in a vertical plane, i.e. the probe head of the apparatus is set up with an inclination upwards or downwards.

Figure 2:
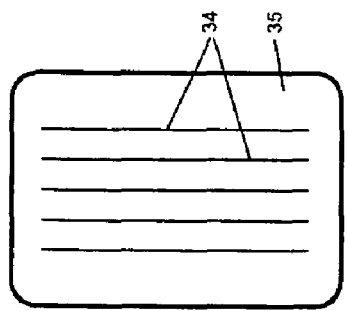
FIG. 2 shows a schematic front view of the object under test.
Figure 3:
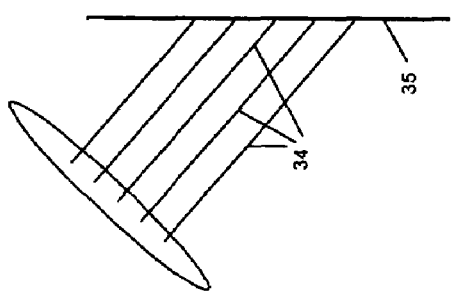
FIG. 3 shows a schematic top view of a line pattern projected from an alternative illumination device.

A further embodiment of the present invention makes use of a means for visualizing a possible angular error in setting up the probe head 6 of the apparatus such that the position and orientation, respectively, of the probe head 6 of the apparatus can be easily corrected before the measurement is taken. To this end, the further embodiment of the invention provides an alternative illumination device, a portion thereof being shown purely schematical in FIG. 3, to project, under an angle of 45°, a line pattern onto the surface of the object under test. As can be seen in FIG. 2, the parallel lines 34 of the line pattern run vertically on the object under test 35.

Figure 4:
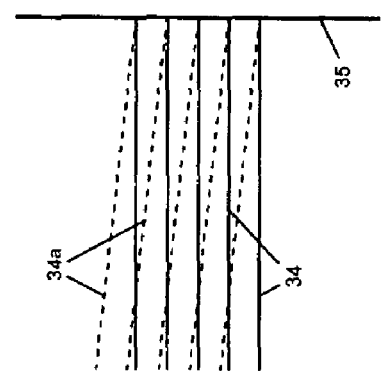
FIG. 4 shows a schematic side view of a line pattern projected on an object under test with an angular error.

If the probe head 6 of the apparatus is set up with an angular error, as indicated in FIG. 4 by the dashed lines 34*a*, the resulting line pattern 34*a* on the surface of the object under test 35 are inclined as compared to the vertically line pattern 34 created by a correctly set up portable apparatus.

The line pattern 34 and 34*a*, respectively, can be captured by means of the lens 26 and the sensor 25 and made visible on the display 4 (FIG. 1). In this way, the operator can correct the position and orientation, respectively, of the probe head 6 of the apparatus. On the other hand, the picture captured by the sensor 25 can be processed by the microprocessor controller 3 to calculate the misalignment on the basis of the angle of the lines 34*a* projected to the object under test. This is directly proportional to the angle of the optical axis of the probe head 6 of the apparatus. Thus, the controller 3 can output an indication useful for the operator to correct the angular position of the probe head 6 of the apparatus.

In the apparatus described herein before and further explained with reference to FIG. 1, there is already an illumination assembly 1 adapted for performing the measurement of the color stimulus specification and illuminating the object under test under an angle of 45°. Thus, it is obvious to use at least parts of this illumination assembly for projecting the line array 34 onto the surface of the object under test 35. In order not to interfere with the colorimetric measurement by projecting the line array 34 onto the surface of the object under test 35, for the colorimetric measurement, the illumination must be homogenous, the line array 34 is generated in the region of infrared light.

Figure 6:
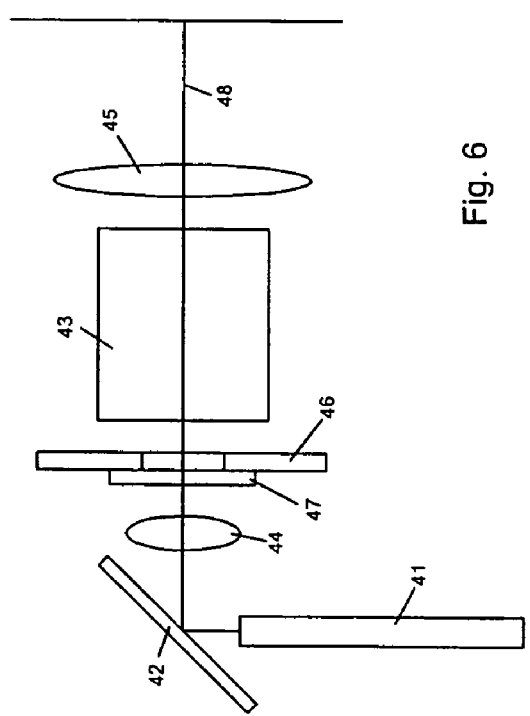
FIG. 6 shows a schematic side view of an alternative illuminating device.
Figure 7:
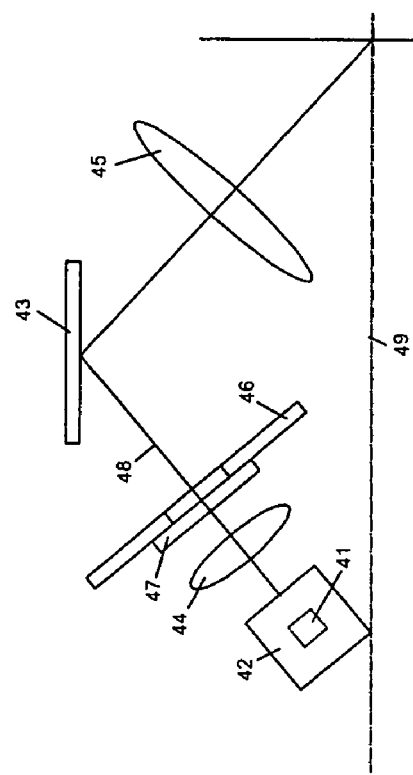
FIG. 7 shows a schematic top view of the alternative illuminating device.

An alternative illumination device is schematically shown in FIG. 6 in a side view and in FIG. 7 in a top view. It comprises a homogenization device 41, for example a glass rod or a fiber bundle, a first redirecting mirror 42, a second redirecting mirror 43, a first lens 44, a second lens 45, a slit diaphragm 46, and a filter 47. The light path is symbolized by line 48, and the dash-dot line in FIG. 7 indicates the symmetry plane. It is understood that it further comprises most of the parts and elements essential for performing the measurement of the color stimulus specification, these parts and elements being shown in and having been discussed in connection with FIG. 1 herein before.

With regard to the illumination device 1 shown in FIG. 1, the alternative illumination device shown in FIGS. 6 and 7 show the following differences:

The LED array 14 (not shown in FIGS. 6 and 7) additionally comprises at least one light emitting diode emitting light in the proximal infrared region (wavelength around 850 nm). The IR light emitted by this or these light emitting diode(s) is captured also by the fiber optic bundle 41. Moreover, besides the afore mentioned eight consecutive measurements with eight different wave-lengths, a further measurement with illumination by the additional IR light emitting diode or light emitting diodes is made.

Figure 5:
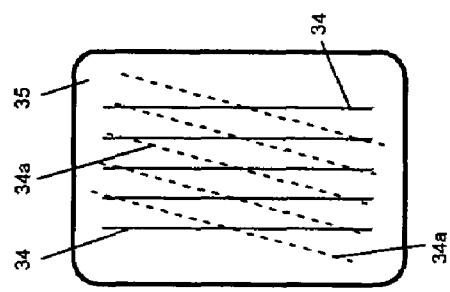
FIG. 5 shows another schematic front view of the object under test.

The fiber optic bundle 41 is not split into two strands 17a, 17b. Instead, the light beam leaving the fiber optic bundle 41 is redirected by means of the first mirror 42 by 90°. The front side of the mirror 42 is provided with a so-called cold light mirror layer. Such a layer acts as a mirror for all visible light, but is transparent for infrared light. The rear surface of the mirror is provided with a line pattern adapted to reflect the infrared light. Thus, this line pattern is projected, through the front side layer of the mirror 42 being transparent for IR radiation, and via the redirecting mirror 43 and the lens 45, to the object under test 35. The line pattern is directed such that it runs in vertical direction on the surface of the object under test, as shown in FIGS. 2 and 5.

In order to ensure that the line pattern is displayed on the surface of the object under test 35 in focus, a filter/diaphragm assembly 46, 47 is inserted into the light path 48. This is necessary because the reflective line pattern at the rear side of the mirror 42 is not exactly at the correct position, resulting in an unsharp picture of the line pattern on the surface of the object under test 35. By means of the slotted diaphragm 46, the depth of field is increased by such an amount that a sharp picture of the line pattern results.

Again, the slotted diaphragm 46 is designed such that it is not effective for visible light, i.e. transparent, in order to avoid a loss of light energy. This is realized again by means of a so-called cold light mirror surface layer, having a central slot. Thus, the visible light can pass through the filter/diaphragm 45/46 unimpededly, while infrared light can pass only through the slotted area. If it should happen that traces of the line pattern are present in the visible band, because the cold light mirror surface is not perfect, they do not harm because they would be completely out of focus.

It is understood that the illumination device shown in FIGS. 6 and 7 is symmetrical regarding the line 49. However, the projection of the line pattern onto the object under test 35 may be done only from one side. Therefore, the symmetrical portion, not shown in the drawings, is designed slightly different. The first mirror 42 does not have any reflective layer, particularly no line pattern, on its rear surface. Consequently, no infrared light is projected onto the surface of the object under test 35 from that side. Moreover, the assembly 45, 46 is a cold light mirror without slot and, thus, not transparent for infrared light. Thus, light in the infrared wavelength region comes only from one side, while visible light is projected onto the surface of the object under test 35 from both sides.

Moreover, it is understood, even if a light conducting fiber bundle is mentioned herein before as a light conducting means, any other suitable light conducting means, such as a glass rod or bar or a rod or bar made of a transparent plastic material could be used. Another option within the scope of the present invention is to make use of ultra violet light to project a line pattern onto the object under test, instead of infrared light. The only requirement for the wavelength of the light used to project a line pattern onto the object under test is that it is outside of the wavelength of the visible light used for measuring the color stimulus specification of the object under test.

What is claimed is:

1. An apparatus for determining the color stimulus specification of translucent objects, comprising:
an illumination assembly for illuminating the object under test;
a detection assembly for capturing the light emitted by said illumination assembly and reflected by said object under test, said detection assembly including a lens and an image sensor and adapted to deliver output signal data in response to the captured light;
at least one first polarizing filter configured to polarize the light emitted by said illumination assembly;
a second polarizing filter configured to polarize light received by said detection assembly, whereby said first and said second polarizing filters are oriented relative to each other to suppress the light reflected by the surface of the object under test;
a display for visualizing said output signal data delivered by said detection assembly; and
a control and analyzer device adapted for evaluating the colorimetric data of said object under test;
said illumination assembly including a light emitting diode array including a plurality of light emitting diodes emitting light in different wave length portions, each light emitting diode or group of light emitting diodes emitting light in a certain wave length portion being sequentially energized under the influence of said control and analyzer device.

2. An apparatus according to claim 1 in which said light emitting diode array comprises at least six different types of light emitting diodes emitting visible light in six different wave length portions, whereby the particular types of light emitting diodes are sequentially energized.

3. An apparatus according to claim 1 in which said light emitting diodes of said array are arranged along a circle or an annulus.

4. An apparatus according to claim 1 in which said light emitting diodes of said array are arranged on a metal core circuit board by means of chip-on-board technology.

5. An apparatus according to claim 1 in which the light emitted by said light emitting diodes of said array has a wave length bandwidth of between 25 nm and 100 nm.

6. An apparatus according to claim 1 in which multiple light emitting diodes are connected in parallel or energized in parallel for particular wave length regions.

7. An apparatus according to claim 1 in which said detection assembly comprises at least one black-and-white image sensor for capturing the images in the different wave length regions, whereby the object under test is sequentially illuminated by means of three different types of light emitting diodes emitting light in the three wave length regions that determine the three primary colors red, green and blue, and whereby the three images captured by the sensor in those three primary colors are combined and shown on said display as a color image.

8. An apparatus according to claim 1 in which the light emitted by the light emitting diode array is fed to the input side of a light conducting fiber bundle and projected through a lens onto the object under test in such a way that an area of at least 10 mm×15 mm is substantially evenly illuminated.

9. An apparatus according to claim 8 in which said at least one first polarizing filter is provided at the output of said light conducting fiber bundle.

10. An apparatus according to claim 9, wherein said second polarizing filter is located in front of said image sensor.

11. Apparatus according to claim 1, designed as a portable device and powered by means of batteries.

12. A method for determining the color stimulus specification of translucent objects comprising the steps of:
   illuminating the object under test by;
      providing a light emitting diode array including a plurality of light emitting diodes emitting light in different wave length portions; and
      illuminating said object under test by consecutively energizing each of said light emitting diodes emitting light in different wave length portions;
   capturing the light reflected by said object under test with at least one image sensor;
   suppressing the light reflected by the surface of said object under test;
   arithmetically evaluating the colorimetric data of said object under test by means of a suitable analyzer means; and
   generating an output signal or a display of the results of the evaluation.

13. A method according to claim 12 in which each of said light emitting diodes emitting light in different wave length portions is energized during a period of 10 ms to 30 ms with a multiple of their rated operating current.

14. A method according to claim 13 in which each of said light emitting diodes emitting light in different wave length portions is individually energized in dependence of its efficiency and/or its current carrying capacity.

15. A method according to claim 12 in which both the light emitted by said light emitting diodes emitting light in different wave length portions and the light sent back by said object under test are polarized, whereby the direction of polarization is different to suppress the light reflected by the surface of the object under test.

16. A method according to claim 12 in which an area on the object under test is illuminated that is larger than the area captured by the picture sensor and larger than the area that is significant for the determination of the color stimulus specification of the object under test.

17. A method according to claim 12 in which the object under test is sequentially illuminated by means of three different types of light emitting diodes emitting light in the three primary colors red, blue and green, whereby the three partial images captured by the image sensor are mathematically processed to create a color picture to be displayed on a display.

* * * * *

UNITED STATES PATENT AND TRADEMARK OFFICE
CERTIFICATE OF CORRECTION

| | | |
|---|---|---|
| PATENT NO. | : 7,312,874 B2 | Page 1 of 1 |
| APPLICATION NO. | : 11/173272 | |
| DATED | : December 25, 2007 | |
| INVENTOR(S) | : Berner | |

It is certified that error appears in the above-identified patent and that said Letters Patent is hereby corrected as shown below:

Col. 1, line 14 replace "calorimetric" with --colorimetric--
Col. 1, line 22 replace "calorimetric" with --colorimetric--
Col. 1, line 67 replace "calorimetric" with --colorimetric--
Col. 2, line 29 replace "calorimetric" with --colorimetric--

Signed and Sealed this

Thirteenth Day of May, 2008

JON W. DUDAS
*Director of the United States Patent and Trademark Office*